(12) United States Patent
Sims et al.

(10) Patent No.: US 9,347,894 B2
(45) Date of Patent: May 24, 2016

(54) METHODS AND SYSTEMS FOR PRODUCING VISIBLE LIGHT AND X-RAY IMAGE DATA

(75) Inventors: Gary R. Sims, Tucson, AZ (US);
Michael B. Nelson, Tucson, AZ (US);
Michael D. Cable, Tucson, AZ (US)

(73) Assignee: Spectral Instruments Imaging, LLC, Tucson, AZ (US)

( * ) Notice: Subject to any disclaimer, the term of this patent is extended or adjusted under 35 U.S.C. 154(b) by 1110 days.

(21) Appl. No.: 13/222,633

(22) Filed: Aug. 31, 2011

(65) Prior Publication Data

US 2012/0051514 A1 Mar. 1, 2012

Related U.S. Application Data

(60) Provisional application No. 61/379,261, filed on Sep. 1, 2010.

(51) Int. Cl.
*G01N 23/04* (2006.01)
*A61B 5/00* (2006.01)
*A61B 6/00* (2006.01)
(Continued)

(52) U.S. Cl.
CPC ............ *G01N 23/046* (2013.01); *A61B 5/0035* (2013.01); *A61B 5/0071* (2013.01); *A61B 6/4417* (2013.01); *A61B 6/508* (2013.01); *A61B 6/5247* (2013.01); *G01N 21/6456* (2013.01);
(Continued)

(58) Field of Classification Search
CPC .. A61B 5/0035; A61B 5/0071; A61B 6/4417; A61B 6/508; A61B 6/5247; G01M 21/6456; G01N 21/76; G01N 23/046; G01N 21/6456

USPC .......................................................... 378/63
See application file for complete search history.

(56) References Cited

U.S. PATENT DOCUMENTS 3,800,079 A 3/1974 McNeil et al.
3,871,767 A 3/1975 Holm-Hansen et al.
(Continued)

FOREIGN PATENT DOCUMENTS

EP 0097060 A2 12/1983
EP 0228877 A2 7/1987
(Continued)

OTHER PUBLICATIONS

O'Kane et al., "Absolute Calibration of Luminometers with Low-Level Light Standards," Methods in Enzymology, vol. 305, Copyright 2000 by Academic Press, pp. 87-96.
(Continued)

*Primary Examiner* — David J Makiya
*Assistant Examiner* — Dani Fox
(74) *Attorney, Agent, or Firm* — Fennemore Craig, P.C.

(57) ABSTRACT

An imaging system may include a main enclosure having at least one access door that defines a substantially light-tight imaging compartment when the access door is in a closed position. An object platform provided within the main enclosure holds an object to be imaged. A camera system positioned on a first side of the object platform is operable to capture a visible light image of the object. A radiation detector positioned on the first side of the object platform is moveable from a first position to a second position across a field of view of the camera system. The radiation detector is operable to capture a radiographic image of the object by moving the radiation detector from the first position to the second position while detecting radiation from the object.

18 Claims, 7 Drawing Sheets

(51) Int. Cl.
G01N 21/64 (2006.01)
G01N 21/76 (2006.01)
(52) U.S. Cl.
CPC .......... *G01N 21/76* (2013.01); *G01N 2223/419* (2013.01)

(56) References Cited

U.S. PATENT DOCUMENTS

| | | | |
|---|---|---|---|
| 3,949,162 A | 4/1976 | Malueg | |
| 4,196,994 A | 4/1980 | de Jesus et al. | |
| 4,199,678 A * | 4/1980 | Ladell | 378/75 |
| 4,298,887 A | 11/1981 | Rode | |
| 4,343,021 A | 8/1982 | Frame | |
| 4,585,934 A | 4/1986 | French et al. | |
| 4,593,728 A | 6/1986 | Whitehead et al. | |
| 4,630,202 A | 12/1986 | Mori | |
| 4,687,325 A | 8/1987 | Corby, Jr. | |
| 4,863,690 A | 9/1989 | Berthold et al. | |
| 4,885,544 A | 12/1989 | Tago | |
| 4,948,975 A | 8/1990 | Erwin et al. | |
| 5,008,548 A | 4/1991 | Gat | |
| 5,039,868 A | 8/1991 | Kobayashi et al. | |
| 5,202,091 A | 4/1993 | Lisenbee | |
| 5,401,465 A | 3/1995 | Smethers et al. | |
| 5,414,258 A | 5/1995 | Liang | |
| 5,493,594 A * | 2/1996 | Hamada et al. | 378/34 |
| 5,515,161 A | 5/1996 | Blumenfeld | |
| 5,542,012 A | 7/1996 | Fernandes et al. | |
| 5,587,583 A | 12/1996 | Chin et al. | |
| 5,672,881 A | 9/1997 | Striepeke et al. | |
| 5,680,492 A | 10/1997 | Hopler et al. | |
| 5,689,110 A | 11/1997 | Dietz et al. | |
| 5,818,977 A | 10/1998 | Tansley | |
| 5,840,572 A | 11/1998 | Copeland et al. | |
| 5,865,754 A | 2/1999 | Sevick-Muraca et al. | |
| 5,898,802 A | 4/1999 | Chen et al. | |
| 5,964,220 A | 10/1999 | Boussignac et al. | |
| 5,986,271 A | 11/1999 | Lazarev et al. | |
| 6,004,767 A | 12/1999 | Crouch et al. | |
| 6,038,038 A | 3/2000 | Selby et al. | |
| 6,097,025 A | 8/2000 | Modlin et al. | |
| 6,154,277 A | 11/2000 | Snelling et al. | |
| 6,205,244 B1 | 3/2001 | Bawolek et al. | |
| 6,217,847 B1 | 4/2001 | Contag et al. | |
| 6,377,353 B1 | 4/2002 | Ellis | |
| 6,614,452 B1 | 9/2003 | Cable | |
| 6,642,499 B1 | 11/2003 | Boni et al. | |
| 6,735,274 B1 * | 5/2004 | Zahavi et al. | 378/15 |
| 6,754,008 B1 | 6/2004 | Wallerstein et al. | |
| 6,775,567 B2 | 8/2004 | Cable et al. | |
| 6,894,289 B2 | 5/2005 | Nilson et al. | |
| 6,901,279 B2 | 5/2005 | Cable et al. | |
| 6,919,919 B2 | 7/2005 | Nelson et al. | |
| 6,922,246 B2 | 7/2005 | Nilson et al. | |
| 7,113,217 B2 | 9/2006 | Nilson et al. | |
| 7,116,354 B2 | 10/2006 | Rice et al. | |
| 7,177,024 B2 | 2/2007 | Nilson et al. | |
| 7,190,991 B2 | 3/2007 | Cable et al. | |
| 7,196,190 B2 | 3/2007 | Ning et al. | |
| 7,255,851 B2 | 8/2007 | Contag et al. | |
| 7,298,415 B2 | 11/2007 | Nilson et al. | |
| 7,299,420 B2 | 11/2007 | Cable | |
| 7,331,341 B2 | 2/2008 | Nelson | |
| 7,352,840 B1 | 4/2008 | Nagarkar et al. | |
| 7,383,078 B2 | 6/2008 | Cable et al. | |
| 7,403,812 B2 | 7/2008 | Rice et al. | |
| 7,449,567 B2 | 11/2008 | Zhang et al. | |
| 7,449,615 B2 | 11/2008 | Contag et al. | |
| 7,461,652 B2 | 12/2008 | Dalgetty et al. | |
| 7,464,707 B2 | 12/2008 | Dalgetty et al. | |
| 7,466,418 B2 | 12/2008 | Nilson et al. | |
| 7,474,398 B2 | 1/2009 | Nilson et al. | |
| 7,474,399 B2 | 1/2009 | Nilson et al. | |
| 7,503,323 B2 | 3/2009 | Dalgetty et al. | |
| 7,555,332 B2 | 6/2009 | Rice et al. | |
| 7,555,334 B2 | 6/2009 | Coquoz et al. | |
| 7,581,191 B2 | 8/2009 | Rice et al. | |
| 7,589,786 B2 | 9/2009 | Nilson et al. | |
| 7,595,838 B2 | 9/2009 | Nilson et al. | |
| 7,599,731 B2 | 10/2009 | Rice et al. | |
| 7,603,167 B2 | 10/2009 | Stearns et al. | |
| 7,616,985 B2 | 11/2009 | Stearns et al. | |
| 7,663,664 B2 | 2/2010 | Rice et al. | |
| 7,734,325 B2 * | 6/2010 | Vizard et al. | 600/407 |
| 2001/0028510 A1 | 10/2001 | Ramm et al. | |
| 2003/0039332 A1 | 2/2003 | Bavendiek et al. | |
| 2003/0082104 A1 * | 5/2003 | Mertelmeier | 424/9.4 |
| 2004/0141588 A1 | 7/2004 | Francke et al. | |
| 2006/0064000 A1 * | 3/2006 | Vizard et al. | 600/407 |
| 2007/0238957 A1 * | 10/2007 | Yared | 600/407 |
| 2010/0030069 A1 * | 2/2010 | Peter | 600/427 |

FOREIGN PATENT DOCUMENTS

| | | |
|---|---|---|
| EP | 0491131 A1 | 6/1992 |
| EP | 0493707 A2 | 7/1992 |
| EP | 0718622 A2 | 6/1996 |
| EP | 1478423 B1 | 7/2006 |
| EP | 1478916 B1 | 7/2008 |
| WO | 9400742 A1 | 1/1994 |
| WO | 9908233 A1 | 2/1999 |
| WO | 0049938 A1 | 8/2000 |
| WO | 0161324 A1 | 8/2001 |
| WO | 0163247 A2 | 8/2001 |
| WO | 2010067281 A1 | 6/2010 |

OTHER PUBLICATIONS

Brown et al., "Absolute Radiometric Calibration of Digital Imaging Systems," IS&T/SPIE Electronic Imaging, San Jose, California, Jan. 2001, 9 pages.

Chen et al., "Auaomated Calibration of a Zoom Lens CCD Image System for Videogrammetry," International Archives of Photogrammetry and Remote Sensing, vol. XXXIII, Part B4, Amsterdam, The Netherlands, 2000, pp. 180-185.

Campbell et al., "Bioluminescence and Chemiluminescence," Proceedings of the 8th International Symposium of Bioluminescence and Chemiluminescence, Cambridge, Sep. 1994, John Wiley & Sons, 5 pages.

Contag et al., "Bioluminescent indicators in living mammals," Nature Medicine, vol. 4, No. 2, Feb. 1998, http://www.nature.com/naturemedicine, pp. 245-247.

Ochs et al., "Camera Types for Low Level Light Imaging," Oct. 1995, pp. 1-6.

Gatan, Inc., "CCD Image Acquisition Tutorial," Gatan, Inc., Pleasanton, California, May 2001, cover pages and pp. 1-7.

Haworth, "CCD Image Calibration Using AIP4WIN," http://www.stargazing.net/david, Copyright 2001 David Haworth v. 5.0, pp. 1-12.

Roda et al., "Chemiluminescence Imaging Systems for the Analysis of Macrosamples: Microtiter Format, Blot Membrane, and Whole Organs," Methods in Enzymology, vol. 305, Copyright 2000 by Academic Press, pp. 120-132.

Stanley, "Commercially Available Luminometers and Low-Level Light Imaging Devices," Methods in Enzymology, vol. 305, Copyright 2000 by Academic Press, pp. 96-103.

Ross et al., "High-speed radiometric imaging with a gated, intensified, digitally-controlled camera[2869-29]," http://ucla.worldcat.org, Proceedings—SPIE the International Society for Optical Engineering, No. 2869, (1996): 386-394, British Library Serials, 2 pages.

Rice et al., "In vivo imaging of light-emitting probes," Journal of Biomedical Optics, vol. 6, No. 4, Oct. 2001, pp. 432-440.

Hengerer et al., "In vivo Procedure for the Measurement Luciferase Reporter Gene Activity with a Low Light Imaging System," Reprint from BIOspektrum 4 (1998), pp. 1-3.

Berthold et al., "Luminometer Design and Low Light Detection," Methods in Enzymology, vol. 305, Copyright 2000 by Academic Press, pp. 62-87.

Brauer et al., "Measuring luminescence with a low light level imaging system using electronic light standards," Siemens AG, Karlsruhe,

(56) References Cited

OTHER PUBLICATIONS

Germany, Bioluminescence & Chemiluminescence status report, Chichester:Wiley 1993: 13-17, 1 page.

Szalay et al., "Bioluminescence and chemiluminescence: status report: proceedings of the VIIth Bioluminescence and Chemiluminescence," Banff, Mar. 1993, http://ucla.worldcat.org, 1 page.

Francis et al.,"Monitoring Bioluminescent *Staphylococcus aureus* Infections in Living Mice Using a Novel luxABCDE Construct," http://iai.asm.org/cgi/content/full/68/6/3594, Xenogen Corporation, Alameda, CA and Division of Neonatal andDevelopmental Medicine, Department of Pediatrics, Stanford University Medical Center, Stanford, CA, Infection and Immunity, vol. 68, No. 6, Jun. 2000, cover page and pp. 3594-3600.

Voss et al., "Radiometric and Geometric Calibration of a Visible Spectral Electro-Optic 'Fisheye' Camera Radiance Distribution System," Journal of Atmospheric and Oceanic Technology, vol. 6, (1989), pp. 652-662.

Niles et al., "Radiometric calibration of a video fluorescence microscope for the quantitative imaging of resonance energy transfer," Rev. Sci, Instrum. 66 (6), Jun. 1995, Copyright 1995 American Institute of Physics, pp. 3527-3536.

Edirisinghe et al., "Radiometric Callibration of Multispectral Airborne Video Systems," International Journal of Remote Sensing, vol. 20, No. 14, 1999, cover page and pp. 2855-2870.

Rehemtulla et al.,"Rapid and Quantitative Assessment of Cancer Treatment Response Using In Vivo Bioluminescence Imaging," Neoplasia, vol. 2, No. 6, 2000, www.nature.com/neo, pp. 491-495.

Zhang et al., "Rapid in vivo funtional analysis of transgenes in mice using whole body imaging of luciferase expression," Transgenic Research 10: 2001 Kluwer Academic Publishers, The Netherlands, pp. 423-434.

Tsin et al., "Statistical Calibration of CCD Imaging Process," Appeared in the Proceedings of the IEEE 2001 International Conference on Computer Vision, pp. 1-8.

Contag et al., "Use of Reporter Genes for Optical Measurements of Neoplastic Disease In Vivo," Neoplasia, vol. 2, Nos. 1-2, Jan.-Apr. 2000, www.nature.com/neo, pp. 41-52.

Contag et al., "Visualizing Gene Expression in Living Mammals Using a Bioluminescent Reporter," Photochemistry and Photobiology, 1997, 66(4): pp. 523-531.

International Search Report and Written Opinion for PCT/US2011/049987, dated Dec. 16, 2011, 8 pages.

\* cited by examiner

METHODS AND SYSTEMS FOR PRODUCING VISIBLE LIGHT AND X-RAY IMAGE DATA

CROSS-REFERENCE TO RELATED APPLICATION

This application claims the benefit of U.S. Provisional Patent Application No. 61/379,261, filed on Sep. 1, 2010, which is hereby incorporated herein by reference for all that it discloses.

TECHNICAL FIELD

The present invention relates to x-ray imaging systems in general and more particularly to systems for producing both visible light and x-ray images in molecular imaging applications.

BACKGROUND

Molecular imaging systems are well-known in the art and are used to capture various types or modes of images from any of a wide variety of objects or specimens. Common image types or modes that may be captured by such a device include visible light images, wherein visible light reflected by the object or specimen is captured by a camera associated with the imaging system. In another imaging mode, the visible light comprises light that is emitted by the object itself, as opposed to light that is reflected by the object. In such cases, the emitted light may be generated by a luminescence process, a fluorescence process, or by a combination thereof.

It is also often desirable in such systems to capture an x-ray image of the object. The x-ray image may then be used to correlate or compare certain features and attributes of the object with the visual light image of the same object. Typically, such combination or composite images (i.e., comprising a visible light image as well as an x-ray image) are desirable where the object being imaged is an animal, although the ability to capture such composite images may be desirable in other applications as well.

SUMMARY OF THE INVENTION

An imaging system according to one embodiment of the present invention may include a main enclosure having at least one access door that defines a substantially light-tight imaging compartment when the access door is in a closed position. An object platform provided within the main enclosure holds an object to be imaged. A camera system positioned on a first side of the object platform is operable to capture a visible light image of the object. A radiation detector positioned on the first side of the object platform is moveable from a first position to a second position across a field of view of the camera system. The radiation detector is operable to capture a radiographic image of the object by moving the radiation detector from the first position to the second position while detecting radiation from the object.

Another embodiment of an imaging system according to the teachings of the present invention includes a main enclosure having at least one access door that defines a substantially light-tight imaging compartment when the access door is in a closed position. An object platform provided within the main enclosure holds an object to be imaged. A camera system positioned on a first side of the object platform is operable to capture a visible light image of the object. An x-ray source positioned on a second side of the object platform is operable to direct x-rays toward the second side of the object platform. An x-ray detector positioned on the first side of the object platform is moveable across a field of view of the camera system from a first position to a second position. The x-ray detector is operable to capture an x-ray image of the object by moving the x-ray detector from the first position to the second position while operating the x-ray source to direct x-rays toward the second side of the object platform, x-rays from the x-ray source passing through the object platform and the object positioned on the object platform before being incident on the x-ray detector.

Also disclosed is a method for producing visible light and x-ray images of an object that includes the steps of: Positioning an object to be imaged on an object platform; using a camera located on a first side of the object platform to capture a visible light image of the object; directing x-rays toward a second side of the object platform from an x-ray source located on the second side of the object platform; detecting x-rays passing through the object with an x-ray detector located on the first side of the object platform; and moving the x-ray detector across a field of view of the camera while continuing to direct x-rays toward the second side of the object platform in order to capture a two-dimensional x-ray image of the object.

BRIEF DESCRIPTION OF THE DRAWINGS

Illustrative and presently preferred exemplary embodiments of the invention are shown in the drawings in which.

DETAILED DESCRIPTION OF THE PREFERRED EMBODIMENTS

Figure 1:
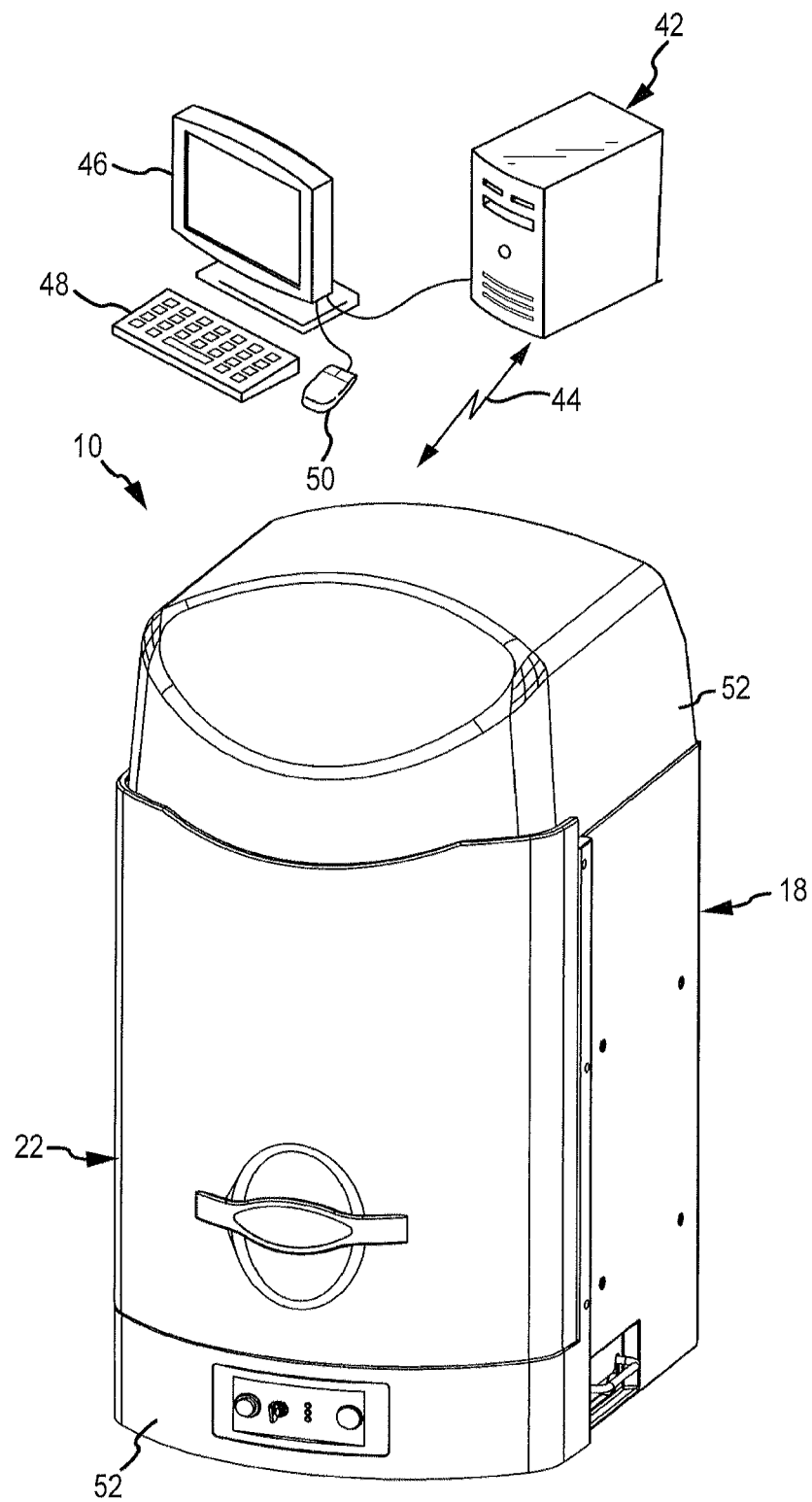
FIG. 1 is a perspective view of one embodiment of a composite imaging system according to the teachings of the present invention.
Figure 2:
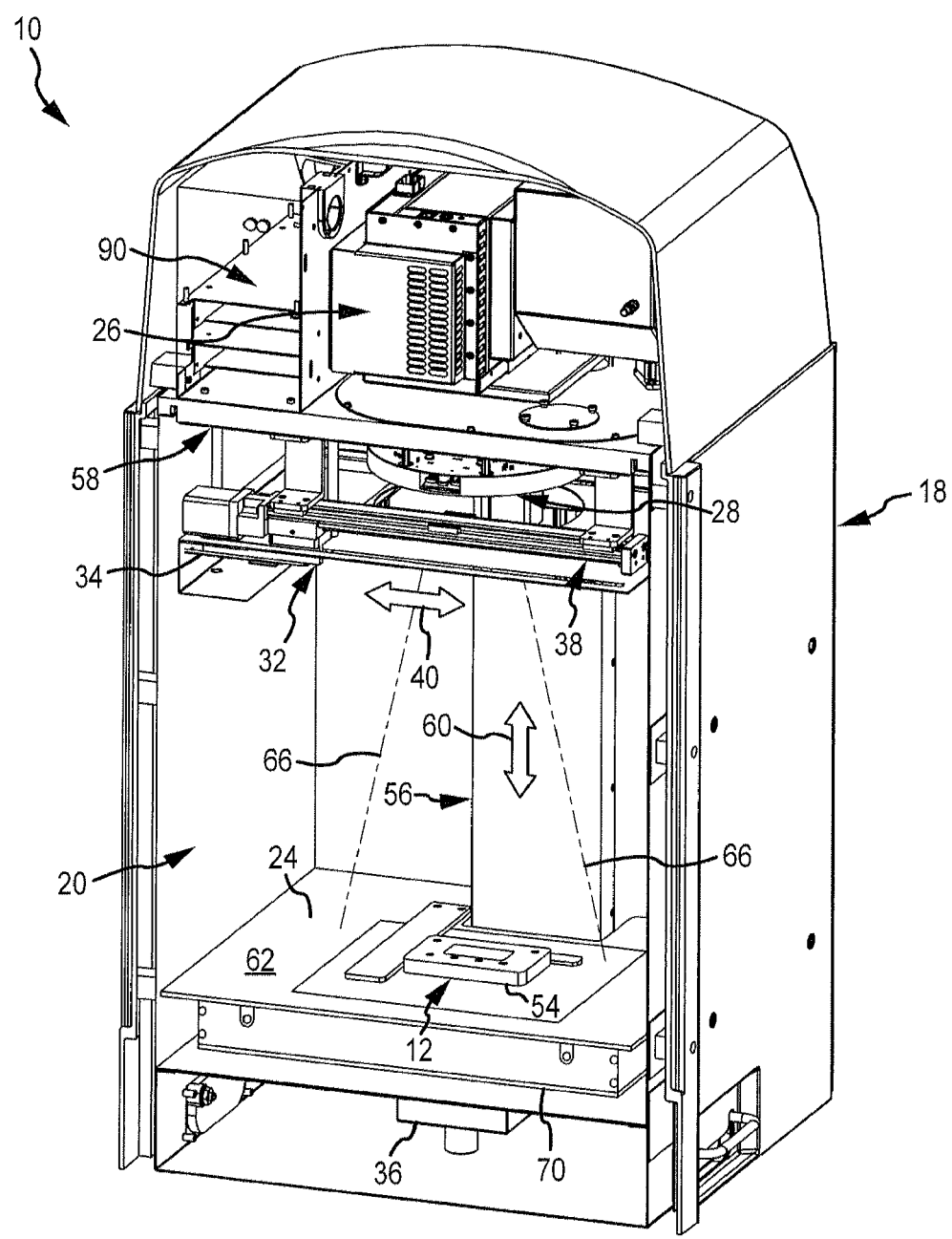
FIG. 2 is a sectional view in perspective of the composite imaging system illustrated in FIG. 1 more clearly showing certain components associated with the visible light and x-ray imaging systems.
Figure 3:
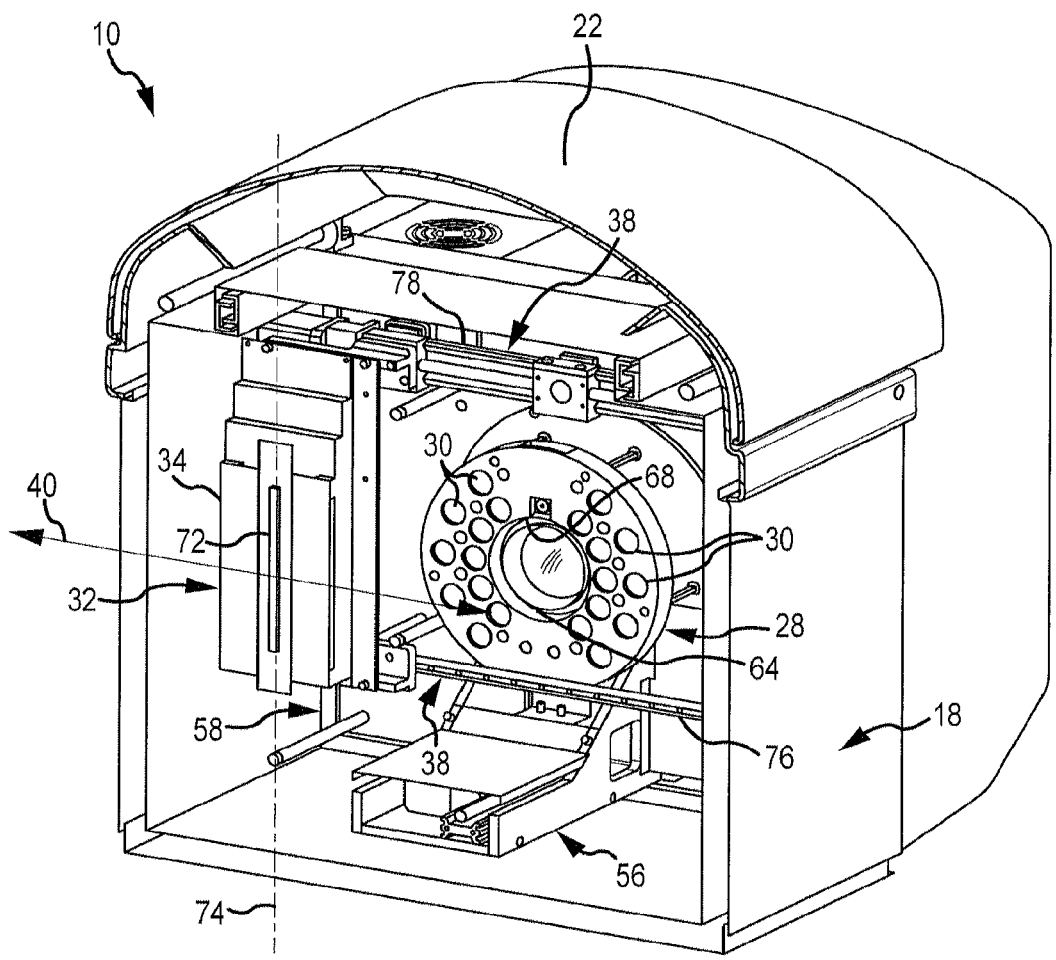
FIG. 3 is a sectional view in perspective of the composite imaging system of FIG. 1 more clearly showing the x-ray detector and gantry assembly.

One embodiment of a composite imaging system 10 (i.e., an imaging system that is operable to capture both visible light and radiographic images of an object) is best seen in FIGS. 1-3 and is shown and described herein as it may be used in a molecular imaging application to capture various types of images of various kinds of objects or specimens 12. For example, in one embodiment, the composite imaging system 10 may be used to capture and display various types of composite images 14, 16 of mammalian specimens, as shown FIGS. 4a and 4b. In particular, the composite image 14 depicted in FIG. 4a comprises superimposed reflected and emitted light images of the mammalian specimens 12, whereas the composite image 16 depicted in FIG. 4b comprises superimposed emitted light and radiographic (e.g., x-ray) images of the mammalian specimens 12. Alternatively, the composite imaging system 10 may be used to capture other types of images from other kinds of specimens 12, as will be described in further detail herein.

Referring back now to FIGS. 1-3, in the particular embodiment shown and described herein, the composite imaging system 10 may comprise a generally rectangularly-shaped housing 18 that defines an imaging compartment 20 therein. The housing 18 of imaging system 10 may be provided with an access door 22 that can be moved vertically between a closed position (shown in FIG. 1) and an opened position (not specifically illustrated in the drawing figures) to allow the user to access the imaging compartment or chamber 20 defined within housing 18. The imaging compartment 20 may be provided with an imaging platform or stage 24 therein that is configured to hold one or more objects or specimens 12 to be studied and imaged. Imaging system 10 may also be provided with a camera system 26 and lighting system 28. Lighting system 28 may be provided with a plurality of individual light sources 30 (FIG. 3) that can be selectively illuminated. As will be described in further detail below, camera system 26 and lighting system 28 may be used together to capture various types of visible light images of the specimen or specimens 12.

Composite imaging system 10 may also be provided with a radiographic or x-ray imaging system 32 that may be used to capture various types of radiographic images, including x-ray images, of the object or specimen 12. In the particular embodiment shown and described herein, x-ray imaging system 32 may comprise a radiation or x-ray detector assembly 34 as well as an x-ray source 36. The x-ray detector assembly 34 and x-ray source 36 are provided on opposite sides of the imaging platform or stage 24, as best seen in FIG. 2. In the particular embodiment shown and described herein, the x-ray detector assembly 34 is moveably mounted to a gantry assembly 38 that allows the x-ray detector assembly 34 to be moved along longitudinal direction (indicated by arrows 40) between a first position (shown in FIGS. 2, 3, 5, and 6) and a second position (not specifically illustrated in the drawing figures) on the opposite side of gantry assembly 38. As will be described in greater detail below, movement of the x-ray detector assembly 34 in the longitudinal direction 40 allows two-dimensional radiographic images to be acquired of the object or specimen 12.

In the particular embodiment shown and described herein, the composite imaging system 10 is designed or configured to be connected to separate computer system 42, e.g., via a suitable data link 44. The computer system 42 may comprise a conventional "PC" type of computer system and may be provided with a display system 46, along with one or more input devices, such as a keyboard 48 and a suitable pointing device, such as a mouse 50. The computer system 42 allows a user to operate the composite imaging system 10 and view on display system 46 images produced by the imaging system 10.

The composite imaging system 10 may be used to capture any of a wide range of visible light images and radiographic images of the object or specimen 12 positioned on the imaging platform or stage 24. However, before proceeding with the description, it should be noted that, as used herein, the term "visible light" refers to light that is commonly regarded as being in the visible light spectrum (i.e., having wavelengths ranging from about 400 nanometers (nm) to about 700 nm). However, "visible light" may also refer to light in the near-infrared and near-ultraviolet ranges as well, i.e., light having wavelengths longer than 700 nm and shorter than 400 nm, respectively. Similarly, the term "visible light image" refers to light images produced by detecting light in the visible light range (i.e., in the near infrared, visible, and near-ultraviolet ranges), but rendered in colors that are visible to the human eye. That is, the term "visible light image" also includes so-called "false" color images, in which the various features depicted in the images may or may not be rendered in the same color as actually reflected or emitted by the object or specimen 12.

It should also be noted that the term "radiographic image" as used herein refers to images resulting from the detection of certain types of short wavelength photon radiation. Generally speaking, such photon radiation will include x-ray radiation (i.e., generally regarded as photon radiation having wavelengths of a few 10's of nm or less). In addition, radiographic may refer to photon radiation having wavelengths that are greater (i.e., longer) than or less (i.e., shorter) than the wavelengths typically associated with x-ray radiation.

Continuing now with the description, one type of visible light image that may be captured by the composite imaging system 10 may comprise a simple reflected light image of the specimen 12. Such a reflected light image may be formed by detecting or capturing ambient light reflected by the specimen 12. Another type of visible light image may comprise an emitted light image. An emitted light image may be formed or obtained by capturing light emitted by the specimen 12 itself, e.g., via luminescence and/or fluorescence processes. Such visible light images of the specimen 12 may be captured or recorded by the camera 26 and displayed on display system 46, if desired.

Radiographic images may be obtained by using the radiation or x-ray detector assembly 34 to detect radiation from the specimen 12. A common type of radiographic image may comprise an x-ray image of the specimen 12, which may be formed by detecting x-rays (e.g., from the x-ray source 36) passing through the specimen 12. Another type of radiographic image may be formed by using the x-ray detector assembly 34 to detect radiation (i.e., of the appropriate wavelength) that may be emitted by radioisotopes or other radioactive substances comprising or otherwise provided in the specimen 12.

Figures 4A, 4B:
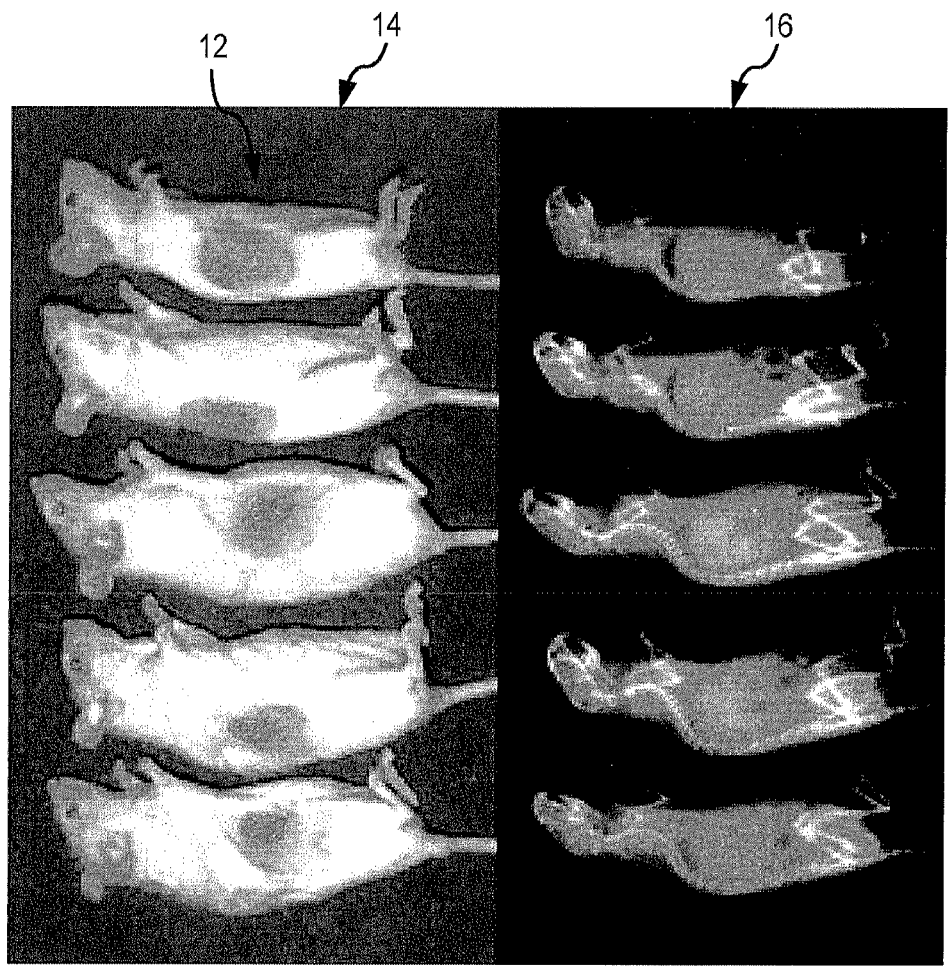
FIG. 4a is a composite image of mammalian specimens comprising reflected and emitted light images.
FIG. 4b is a composite image of the mammalian specimens of FIG. 4a, but comprising emitted light and radiographic images.
Figure 5:
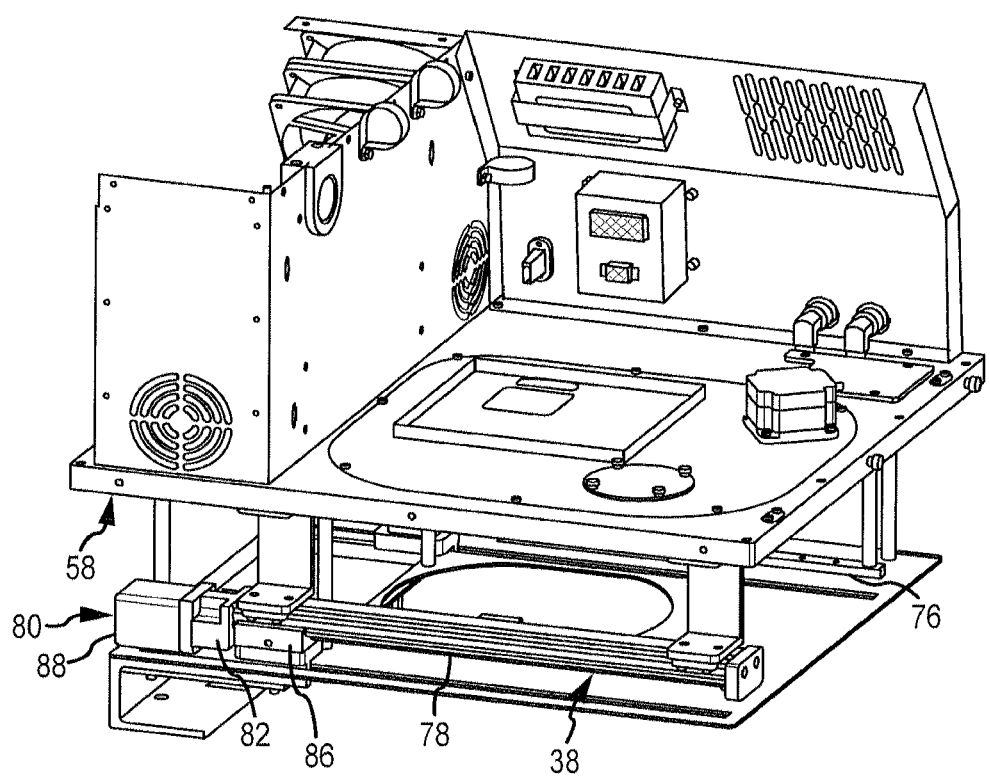
FIG. 5 is an enlarged perspective view of the x-ray detector and gantry assembly.

In many applications, the various types of visible light images (including reflected and emitted light images) and radiographic images (including x-ray and radio-isotopic images) may be combined with one another to form one or more combined or composite images 14 and 16, as shown in FIGS. 4a and 4b. The combined or composite images 14, 16 may also be referred to herein as "overlay" images, in which various combinations of the emitted light, radiographic, and/or reflected light images are superimposed on one another. For example, the composite image 14 depicted in FIG. 4a comprises reflected and emitted light images that are superimposed on one another, whereas composite image 16 depicted in FIG. 4b comprises emitted light and x-ray radiographic images that are superimposed on one another. The composite images provide a visual correlation of the various features and attributes captured by the various types of images. Generally speaking, such composite images are particularly useful when performing in-vivo images of living organisms, although they may be used when studying any type of object or specimen 12, either in-vivo or in-vitro.

The composite imaging system 10 may be used as follows to obtain various types of images (e.g., visible light images and/or radiographic images) of any of a wide variety of specimens 12. In one embodiment, the specimen 12 may comprise a mammalian organism, such as a mouse (depicted in FIGS. 4a and 4b), although in other embodiments, the specimen 12 may comprise a well plate 54 (depicted in FIG. 2) for analyzing chemical samples disposed in the various wells of well plate 54. In any event, and regardless of the particular type of specimen 12 that is to be imaged, once the user has positioned the specimen 12 on the imaging platform or stage 24 (FIG. 2), the access door 22 (FIG. 1) of imaging system 10 may be moved to the closed position. When the access door 22 is closed, the imaging compartment 20 will be dark and substantially light-tight, thereby allowing the camera system 26 to capture a visible light image of the specimen 12.

As briefly described above, the visible light image may comprise a reflected light image of the specimen 12 or an emitted light image produced by luminescent or fluorescent materials comprising the specimen 12. More particularly, if the specimen 12 is luminescent, then camera system 26 may directly capture an emitted light image of the specimen 12 by opening a shutter (not shown) on the camera system 26 for a time sufficient to capture the desired luminescent image. Alternatively, if a fluorescent image of the specimen 12 is to be captured, then the fluorescent material(s) in the specimen 12 may first need to be activated or excited before it will emit substantial amounts of light. The fluorescent material in the specimen 12 may be activated or excited by illuminating the specimen 12 with excitation light of the appropriate wavelength. In the particular embodiment shown and described herein, the excitation light may be provided by activating an individual light source or sources 30 (FIG. 3) of lighting system 28. After an appropriate period of time, the individual light source(s) 30 of lighting system 28 may be extinguished. An emitted light image of the now-fluorescing specimen 12 may be captured by camera system 26.

At some point during the imaging process, e.g., either before or after the capture of the emitted light image by the camera system 26, the imaging system 10 may also capture a reflected light image of the specimen 12. In one embodiment, the reflected light image may also be acquired by camera system 26. Light sufficient for illuminating the specimen 12 may be provided by activating one or more of the light sources 30 of lighting system 28, which may be specifically provided for this purpose.

A radiographic image of the specimen 12 may also be obtained, again either before or after the capture of any desired visible light images. In an embodiment wherein the radiographic image is to comprise an x-ray image of the specimen 12, an x-ray radiographic image may be obtained by operating the x-ray source 36 to produce or otherwise direct x-rays (not shown) toward the specimen 12 provided on platform 24. After passing through the stage 24 and specimen 12, the x-rays are detected by x-ray detector assembly 34. During the x-ray detection process, the detector assembly 34 is activated to detect x-rays passing through the specimen 12. At the same time, the activated detector assembly 34 is moved along the gantry assembly 38, i.e., in the longitudinal direction 40, from the first position on the left-hand side of gantry assembly 38 (i.e., as shown in FIG. 2) to the second position (not shown, on the right-hand side of gantry assembly 38). The movement of the detector assembly 34 along the longitudinal direction 40 during the detection process will allow a two-dimensional x-ray image of the specimen 12 to be produced (e.g., by stitching together various image portions acquired by detector assembly 34 as it is moved along the gantry assembly 38). Thereafter, the x-ray source 36 can be deactivated or otherwise caused to stop directing x-rays toward the specimen 12.

The visible light images (e.g., comprising reflected and/or emitted light images) captured by camera system 26 may be displayed on display system 46 (FIG. 1) operatively associated with the imaging system 10. In one example, a reflected light image of the specimen 12 may be combined with an emitted light image of the specimen 12 to produce a composite image 14 that comprises both the emitted and reflected light images of the specimen 12. See FIG. 4*a*. Similarly, a radiographic image (e.g., comprising an x-ray image) captured by x-ray imaging system 32, may also be displayed on display system 46. In one example, the radiographic image may be combined with one or more images of the other types, such as an emitted light image, to produce a composite image 16, as best seen in FIG. 4*b*.

A significant advantage of the present invention is that both types of images (i.e., visible light images and radiographic images) may be captured nearly simultaneously, typically in rapid succession, thereby eliminating the need to move the specimen or otherwise disturb the imaging system or set-up between image capture modes. In addition, the radiographic (e.g., x-ray) images may also be acquired, processed, and displayed in substantially the same manner (and with the same image processing systems) used for the visible light images.

Still other advantages are associated with the x-ray image detector 34 that may be utilized in the present invention. For example, the x-ray image detector 34 dispenses with the need to use film-based x-ray imaging systems that are typically used in these types of molecular imaging systems. The ability to dispense with such film-based systems allows for the elimination of the cumbersome scintillator plates and film holders associated with conventional systems. In addition, the x-ray image detector 34 generally produces a much higher resolution than do film-based systems. The radiation or x-ray image detector also directly produces image data in the same type of image format (e.g., electronic) as the visible light images produced by the camera system 26. Consequently, subsequent image processing operations and composite image formation steps may be conveniently performed without the need to first develop the x-ray film, then scan the x-ray film to produce electronic image data.

Having briefly described one embodiment of the composite imaging system 10 of the present invention, as well as some of its more significant features and advantages, various exemplary embodiments of the composite imaging system 10 will now be described in detail. However, before proceeding with the description, it should be noted that while the particular embodiments are shown and described herein as they could be used to obtain visible light and radiographic images of certain types of specimens, the particular images and specimens may differ depending on the requirements of the particular imaging application. Consequently, the present invention should not be regarded as limited to the particular specimens, image types, and imaging techniques shown and described herein.

Referring back now primarily to FIGS. 1-3, a composite imaging system 10 according to one embodiment of the present invention may comprise a generally rectangularly-shaped housing or main enclosure 18 that is configured to house and support the various components and subsystems required to perform various types of molecular imaging processes, as will be described herein. The main housing or enclosure 18 may be provided with various external finish panels 52 that cover or overlay the underlying housing or main enclosure structure 18. In the particular embodiment shown and described herein, the composite imaging system 10 is designed or configured to be connected to a separate computer system 42, e.g., via a suitable data link 44, to allow a user to operate the composite imaging system 10 and to view the images produced by the imaging system 10 on a display system 46 associated with computer system 42. Computer system 42 may also be provided with keyboard assembly 48 and a pointing devices, such as a mouse 50, to allow the user to conveniently operate and control the computer system 42 and/or imaging system 10. Alternatively, other arrangements are possible, as would become apparent to persons having ordinary skill in the art after having become familiar with the teachings provided herein. In addition, because computer systems 42 suitable for use with such molecular imaging systems are well-known in the art and could be readily provided by persons having ordinary skill in the art after having become familiar with the teachings provided herein, the particular computer system 42 and associated components will not be described in further detail herein.

The computer system 42 may be provided with one or more software packages or computer programs that allow the computer 42 to interface with the imaging system 10. The computer program(s) may be configured to allow the computer 42 to control various functions and operations of the imaging system 10. In addition, the computer program(s) may be configured to perform various image processing functions to allow the various images (e.g., composite images 14, 16 shown in FIGS. 4a and 4b) to be displayed on display system 46 in the manner described herein.

Software suitable for providing the functionality described herein may be readily provided (e.g., written) by persons having ordinary skill in the art after having become familiar with the teachings provided herein. Consequently, the particular computer programs or software packages that may be provided to computer system 42 will not be described in further detail herein, other than to note those functions and processes that may be implemented thereby.

The main enclosure 18 of composite image system 10 may be provided with an access door 22 that can be moved vertically between a closed position (shown in FIG. 1) and an opened position (not specifically illustrated in the drawing figures) to allow a user to access an imaging compartment 20 defined by the main enclosure 18. See FIG. 2. The imaging compartment or chamber 20 is sized to receive one or more objects or specimens 12 to be imaged. Objects or specimens 12 that may be used with imaging system 10 include samples that may be provided in a well plate 54 as well as living organisms, such as a mouse (depicted in FIGS. 4a and 4b). Other types of objects or specimens 12 may be imaged for other purposes as well, as would become apparent to persons having ordinary skill in the art after having become familiar with the teachings provided herein.

Referring now primarily to FIG. 2, the imaging system 10 also may include an imaging system sub-assembly 56. Sub-assembly 56 may comprise the object platform or stage 24 as well as a mounting or support structure 58. The object platform 24 may be moveably mounted to the sub-assembly 56 so that the object platform 24 can be moved vertically toward and away from the support structure 58, i.e., generally in the directions indicated by arrows 60. The support structure 58 may also be configured to receive camera system 26, lighting system 28, and various components of the radiographic or x-ray imaging system 32.

Support structure 58 may also be configured to receive various other components and systems (e.g., motor and camera control systems as well as a cooling system for the camera system 26) that may be required or desired to capture various kinds of images (e.g., visible and radiographic images) of the specimen 12. However, because a detailed description of such other components and systems is not required to understand and practice the current invention, the particular components and systems that may also be provided to the imaging system 10 will not be described in further detail herein.

Referring now to FIGS. 2 and 3 simultaneously, camera system 26 may be mounted to support structure 58 so that the camera system 26 is located or positioned on a first side 62 of object platform 24 (FIG. 2). The camera system 26 may include a lens assembly 64 (FIG. 3) that defines a field of view (illustrated by lines 66, FIG. 2) that may be substantially coextensive with the imaging platform or stage 24, thereby allowing the camera system 26 to capture a visible light image of the object or specimen 12 provided on the object platform 24. Camera system 26 of imaging system 10 will generally comprise a high-performance, high-sensitivity camera suitable for capturing the extremely low light intensities associated with luminescent or fluorescent objects or specimens 12. During operation, the light sensitive element (not shown) of the camera system 26 is typically cooled to very low temperatures in order to improve the sensitivity, dynamic range, and signal-to-noise ratio of camera system 26.

Camera system 26 of image system 10 may comprise any of a wide range of high-sensitivity cameras that are now known in the art or that may be developed in the future that are or would be suitable for capturing the extremely low light intensities associated with luminescent and/or fluorescent objects or specimens 12. Consequently, the present invention should not be regarded as limited to any particular camera system 26. Camera systems suitable for use as camera system 26 may be obtained from Spectral Instruments, Inc., of Tucson, Ariz.

Referring now primarily to FIG. 3, lighting system 28 is also mounted to support structure 58. In the particular embodiment shown and described herein, lighting system 28 may comprise a generally round or disk-shaped structure that is provided with a central opening 68 therein that is sized to receive the lens assembly 64 of camera system 26. The arrangement is such that the field of view 66 of camera system 26 will be substantially unobstructed by the lighting system 28. Lighting system 28 may be provided with a plurality of individual light sources 30 suitable for illuminating the specimen 12 with light in various desired wavelength regions or bands. More specifically, the light sources 30 may be used to produce excitation light of a wavelength range suitable for exciting the particular fluorescent material in the object 12 to be imaged. Because the imaging system 10 is designed or configured to image a wide variety of fluorescent materials, each of which may require excitation light of a different wavelength or wavelengths, each of the various light sources 30 is configured or designed to produce light in a different wavelength range. Accordingly, a wide range of fluorescent materials may be excited or made to fluoresce by simply activating the particular light source or sources 30 comprising lighting system 28 that produce light in a wavelength range suitable for exciting the particular fluorescent material to be imaged. In the embodiment shown and described herein, several of the individual light sources 30 comprise broad-band (e.g., white light) sources. The broad-band or white light sources may be used to illuminate the object 12 to allow the camera system 26 to capture a reflected light image thereof.

Still referring to FIGS. 2 and 3, various components of the x-ray imaging system 32 also may be mounted to the support structure 58 of imaging system 10. More specifically, and in the embodiment shown and described herein, the x-ray detector 34 and gantry assembly 38 are mounted to the support structure 58. Accordingly, the x-ray detector 34, like camera system 26, is also located or positioned on the first side 62 of object platform 24. X-ray source 36 is mounted on the second side 70 of the object platform 24, generally on the bottom or lower section of imaging system 10, as best seen in FIG. 2. When activated, the x-ray source 36 directs x-rays (not shown) toward the second side 70 of the object platform 24.

X-ray source 36 may comprise any of a wide range of x-ray sources that are now known in the art or that may be developed in the future that are, or would be, suitable for the intended application. Consequently, the present invention should not be regarded as limited to any particular type of x-ray source. However, by way of example, in one embodiment, x-ray source 36 may comprise an x-ray source available from Newton Scientific, Inc., of Cambridge, Mass. (US), as model no. NS-291.

With reference now primarily to FIGS. 3 and 5-7, the x-ray detector 34 may comprise an x-ray sensor element 72 that extends along a transverse direction 74. The x-ray detector 34 (and sensor element 72) is moveably mounted to the gantry assembly 38 that is mounted to support structure 58 of imaging system 10. The gantry assembly 38 allows the x-ray detector 34 to be moved or translated in a longitudinal direction 40 that is generally perpendicular to the transverse direction 74. More specifically, in the particular embodiment shown and described herein, the x-ray detector 34 is moveable between a first position, e.g., on the left side of the camera lens assembly 64 (which position is illustrated in FIGS. 2, 3, 5, and 6), and a second position, e.g., on the right side of the camera lens assembly 64. Thus, the x-ray detector 34 (and sensor element 72) is moveable in the longitudinal direction 40, across the field of view 66 (FIG. 2) of camera system 26.

The x-ray detector 34 may comprise any of a wide range of x-ray detectors that are now known in the art or that may be developed in the future that are, or would be, suitable for the intended application. Consequently, the present invention should not be regarded as limited to any particular type of x-ray detector 34. However, by way of example, in one embodiment, the x-ray detector 34 comprises an x-ray sensor available from Hamamatsu Photonics of Japan. This particular x-ray detector comprises a relatively long, narrow or strip-like sensor element 72 that comprises 4096 picture elements or "pixels" in the long direction (i.e., along transverse direction 74) and 128 pixels in the short direction (i.e., along the longitudinal direction 40). As will be described in greater detail below, in one embodiment the detector 34 is operated in a time delay integration mode in which the light is shifted among the various pixels of the sensor element 72 at the same rate as the detector assembly 34 is moved in the longitudinal direction 40.

Figure 6:
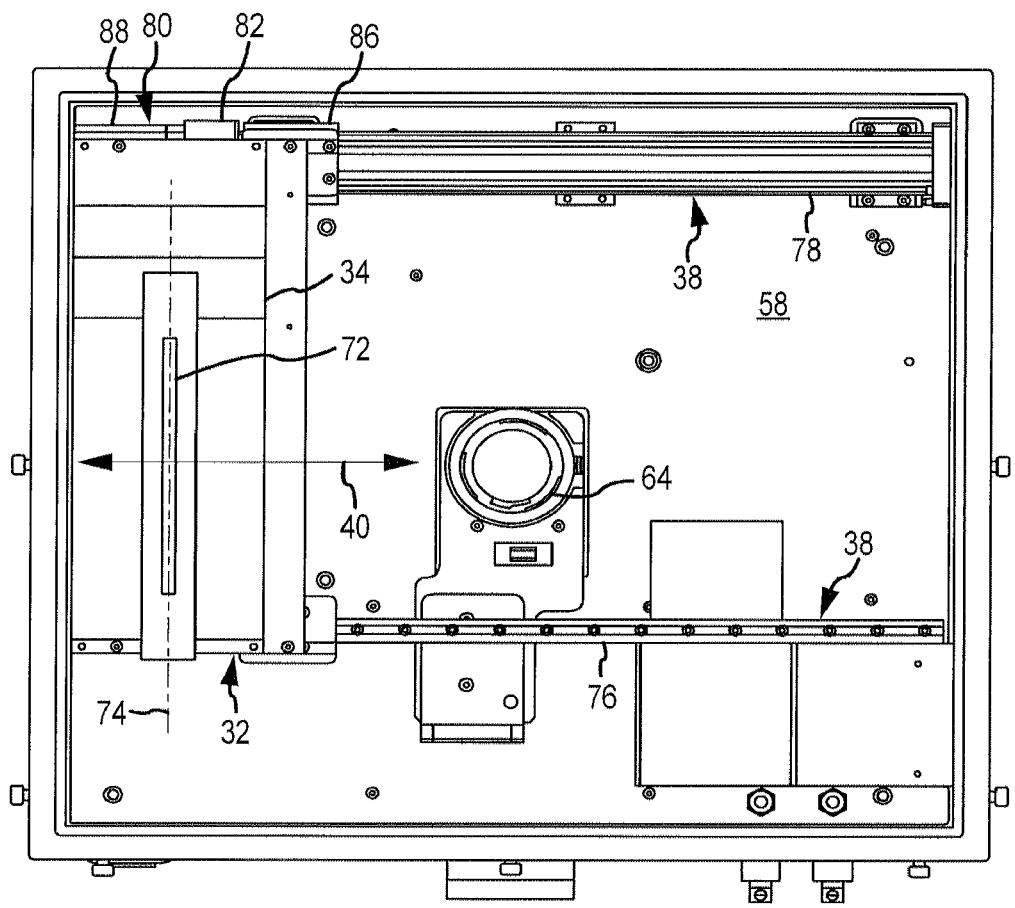
FIG. 6 is a bottom view of the x-ray detector and gantry assembly illustrated in FIG. 5 with the shield plate removed to more clearly show the gantry assembly.
Figure 7:
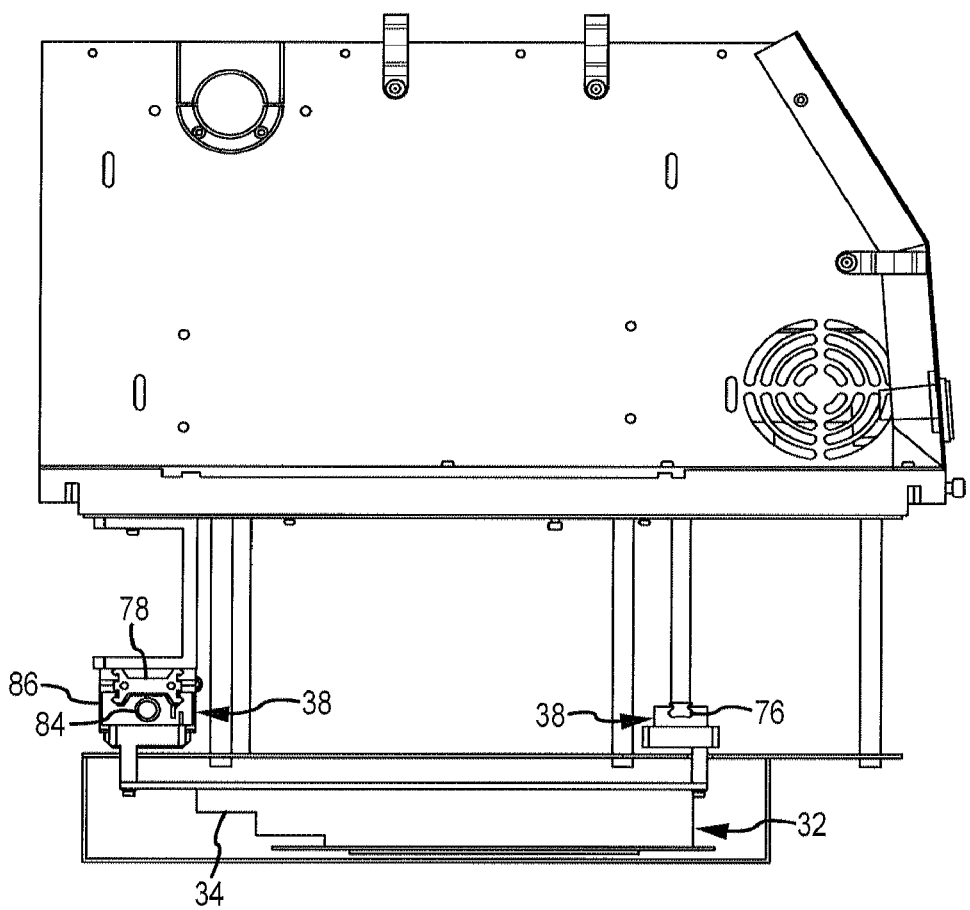
FIG. 7 is a side view of the x-ray detector and gantry assembly illustrated in FIG. 5.

Referring now to FIGS. 6 and 7, the x-ray detector 34 is mounted to gantry assembly 38 that, in one embodiment, may comprise a pair of guide members or guide rails 76, 78 that are mounted to sub-assembly 58 so that they are located in generally parallel, spaced-apart relation. An actuator system 80 operatively associated with the x-ray detector assembly 34 is used to move or translate the x-ray detector 34 along the guide rails 76, 78, between the first and second positions. The actuator system 80 may also comprise a position sensor 82 that is operatively associated with the x-ray detector assembly 34. The position sensor 82 senses a longitudinal position of the x-ray detector assembly 34 along the guide rails 76, 78.

In one embodiment, the actuator system 80 comprises a lead screw 84 mounted for rotation on guide rail 78. See FIG. 7. A lead screw follower or nut 86 mounted to the x-ray detector 34 and engaged with lead screw 84 moves the x-ray detector 34 along the guide rails 76, 78 (i.e., in longitudinal direction 40) in response to rotation of the lead screw 84. A drive motor 88 operatively connected to lead screw 84 rotates lead screw 84, thereby causing the x-ray detector 34 to move along the guide rails 76, 78 in the longitudinal direction 40 in the manner already described.

The position sensor 82 may comprise a rotary encoder (not shown) operatively connected to the lead screw 84 that produces an output signal relating to the rotation of the lead screw 84. Alternatively, a linear encoder or sensor may be used to sense linear movement or translation of the x-ray detector 34 along the guide rails 76, 78.

Referring back now to FIGS. 1 and 2, the composite imaging system 10 of the present invention may also comprise an image data processing system 90, portions of which (e.g., hardware) may be provided within the imaging system 10 itself, and other portions of which (e.g., software) may be provided on computer system 42. The image data processing system 90 may be operatively associated with the x-ray detector system 34 and may process or stitch together various image portions or segments produced by the x-ray detector system 34 (e.g., operated in the time delay integration mode) to form a two-dimensional x-ray image of the object or specimen 12. The image data processing system 90 may also be operatively associated with the actuator system 80, the position sensing system 82, and the x-ray source 36. The image data processing system 90 may operate those systems in conjunction with the x-ray detector system 34 in accordance with the methods described herein in order to capture an x-ray image of the object 12. The image data processing system 90 may also be operatively associated with the camera system 26 and lighting system 28 and may be used to process visible light images captured from the camera system 26 as well.

The composite imaging system 10 may be operated as follows to capture both visible light images and x-ray images of an object or specimen 12 positioned on the object platform 24. In one embodiment, the image data processing system 90 may be programmed or operated to control the various elements and devices in the manner described to perform the various steps in the methods described herein. Alternatively, other operational architectures are possible, as would become apparent to persons having ordinary skill in the art after having become familiar with the teachings provided herein. Consequently, the present invention should not be regarded as limited to the particular operational architecture described herein.

A visible light image of the object 12 may be captured after the user has closed the door 22 to the composite imaging system 10. Lighting system 28 may be used to illuminate the object 12 in order to capture a reflected light image of the object 12. Alternatively, a visible light image of light being emitted by the object 12 itself, e.g., as a result of luminescence or fluorescence, may be obtained by allowing the camera system 26 to detect a sufficient number of photons from the object 12. During visible light imaging, the x-ray detector system 34 will remain in either the first position or the second position so as not to obstruct the field of view 66 of camera system 26.

A radiographic image, such as an x-ray image, of the object 12 may be captured or obtained by activating the x-ray source 36 located on the second side 70 of the object platform 24. The radiographic (e.g., x-ray) image may be obtained either prior to or after the visible light image process described above. During the radiographic imaging process, the activated x-ray source 36 will direct x-rays (not shown) toward the second side 70 of the object platform 24. Thereafter, the x-rays will penetrate the object platform 24 as well as the object 12 provided thereon. The x-ray detector 34 will detect x-rays passing through the object platform 24 and the object 12. As mentioned above, in one embodiment the x-ray detector 34 is operated in a time delay integration mode in which the light is shifted across the various pixels of sensor element 72 at the same rate as the detector 34 is moved in the longitudinal direction 40. Operation in such a time delay integration mode will allow the detector 34 to acquire or integrate more radiation from the specimen 12, thereby improving the quality of the resultant image data. The detector 34 will continue to detect such x-rays as it is moved or translated (i.e., in longitudinal direction 40) from the first position to the second position, across the field of view 66 of camera system 26. In so doing, a two-dimensional x-ray image may be constructed by combining or stitching together the plurality of image portions or segments obtained by the x-ray detector 34 as it moves along the longitudinal direction 40.

As described above, the various image types (e.g., visible and radiographic) of a specimen or specimens 12 captured by the imaging system 10 may be displayed on the display system 46 (FIG. 1). In particular, visible light images (e.g., comprising reflected and/or emitted light images) captured by camera system 26 may be displayed on display system 46. In one example application, a reflected light image of specimens 12 may be combined with an emitted light image of specimens 12 to produce a composite image 14 that comprises both the emitted and reflected light images. See FIG. 4a. Similarly, a radiographic image (e.g., comprising an x-ray image) captured by x-ray imaging system 32, may also be displayed on display system 46. In one example application, the radiographic image may be combined with one or more images of the other types (e.g., an emitted light image) to produce a composite image 16, as best seen in FIG. 4b.

Having herein set forth preferred embodiments of the present invention, it is anticipated that suitable modifications can be made thereto which will nonetheless remain within the scope of the invention. The invention shall therefore only be construed in accordance with the following claims:

The invention shall therefore only be construed in accordance with the following claims:

1. An imaging system, comprising:
   a main enclosure having at least one access door, said main enclosure defining a substantially light-tight imaging compartment when the access door is in a closed position;
   an object platform provided within said main enclosure for holding an object to be imaged;
   a camera positioned on a first side of said object platform, said camera captures a visible light image of the object; and
   a radiation detector positioned on the first side of said object platform, said radiation detector being moveable across a field of view of said camera from a first position to a second position, said radiation detector captures a radiographic image of the object by moving said radiation detector from the first position to the second position while operating said detector to detect radiation from said object.

2. The imaging system of claim 1, wherein said radiation detector comprises an x-ray detector and wherein said imaging system further comprises an x-ray source positioned on a second side of said object platform, said x-ray source being operable to direct x-rays toward the second side of said object platform, said x-ray detector being operable to capture an x-ray image of the object by moving said x-ray detector from the first position to the second position while operating said x-ray source to direct x-rays toward the second side of said object platform, x-rays from said x-ray source passing through said object platform and the object positioned on said object platform before being incident on said x-ray detector.

3. The imaging system of claim 2, further comprising an image processing system operatively associated with said camera and said x-ray detector, said image processing system processing image data produced by said camera and said x-ray detector to produce a composite image, said composite image comprising portions of image data produced by said camera and image data produced by said x-ray detector.

4. The imaging system of claim 3, wherein the image data produced by said camera and said x-ray detector comprise electronic image data.

5. The imaging system of claim 1, further comprising a gantry assembly mounted to said imaging system and wherein said radiation detector is mounted to said gantry assembly so that said radiation detector is moveable along said gantry assembly in a longitudinal direction.

6. The imaging system of claim 5, wherein said gantry assembly further comprises:
   a first guide rail mounted to said imaging system so that said first guide rail extends along the longitudinal direction; and
   a second guide rail mounted to said imaging system, said second guide rail being in generally parallel, spaced-apart relation to said first guide rail.

7. The imaging system of claim 6, further comprising an actuator system operatively associated with said gantry assembly and said radiation detector, said actuator system operable to move said radiation detector along said gantry assembly from the first position to the second position.

8. The imaging system of claim 7, wherein said actuator system comprises:
   a lead screw mounted for rotation with respect to said second guide rail;
   a lead screw follower engaged with said lead screw and slidably mounted to said second guide rail, said lead screw follower also being mounted to said radiation detector; and
   a motor operatively associated with said lead screw, said motor rotating said lead screw.

9. The imaging system of claim 5, further comprising a position sensor operatively associated with said radiation detector and said gantry assembly, said position sensor sensing a position of said x-ray sensor along the longitudinal direction.

10. An imaging system, comprising:
    a main enclosure having at least one access door, said main enclosure defining a substantially light-tight imaging compartment when the access door is in a closed position;
    an object platform provided within said main enclosure for holding an object to be imaged;
    a camera positioned on a first side of said object platform, said camera captures a visible light image of the object;
    an x-ray source positioned on a second side of said object platform, said x-ray source being operable to direct x-rays toward the second side of said object platform; and
    an x-ray detector positioned on the first side of said object platform, said x-ray detector being moveable across a field of view of said camera from a first position to a second position, said x-ray detector captures an x-ray image of the object by moving said x-ray detector from the first position to the second position while operating said x-ray source to direct x-rays toward the second side of said object platform, x-rays from said x-ray source passing through said object platform and the object positioned on said object platform before being incident on said x-ray detector.

11. The imaging system of claim 10, wherein said x-ray detector further comprises:
- at least one guide member mounted to said main enclosure;
- an x-ray sensor mounted to said at least one guide member, said x-ray sensor being moveable along said at least one guide member from the first position to the second position;
- an actuator system operatively associated with said x-ray sensor, said actuator system operable to move said x-ray sensor along said at least one guide member; and
- a position sensor operatively associated with said x-ray sensor, said position sensor sensing a position of said x-ray sensor.

12. The imaging system of claim 11, wherein said x-ray sensor extends along a transverse direction and wherein said at least one guide member extends along a longitudinal direction that is substantially perpendicular to the transverse direction, said actuator moving said x-ray sensor along the longitudinal direction.

13. The imaging system of claim 11, wherein said actuator comprises:
- a lead screw mounted for rotation on said main enclosure;
- a lead screw follower mounted to said x-ray sensor, said lead screw follower operatively engaging said lead screw; and
- a motor operatively associated with said lead screw, said motor rotating said lead screw.

14. The imaging system of claim 10, further comprising an image data processing system operatively associated with x-ray detector, said image data processing system producing two-dimensional x-ray image data from a plurality of x-ray image data.

15. A method for producing visible light and x-ray images of an object, comprising:
- positioning an object to be imaged on an object platform;
- using a camera located on a first side of the object platform to capture a visible light image of the object;
- directing x-rays toward a second side of the object platform from an x-ray source located on the second side of the object platform;
- detecting x-rays passing through the object with an x-ray detector located on the first side of the object platform; and
- moving the x-ray detector across a field of view of the camera while continuing to direct x-rays toward the second side of the object platform in order to capture a two-dimensional x-ray image of the object.

16. The method of claim 15, wherein the x-ray detector detects x-rays along a transverse direction and wherein said moving comprises moving the x-ray detector along a longitudinal direction that is substantially perpendicular to the transverse direction.

17. A method of producing visible light and radiographic images of an object, comprising:
- positioning an object to be imaged on an object platform;
- using a camera located on a first side of the object platform to capture a visible light image of the object;
- detecting radiation emitted by a radioisotope provided in the object with a radiation detector located on the first side of the object platform; and
- moving the radiation detector across a field of view of the camera while continuing to detect radiation emitted by the radioisotope in the object in order to capture a two-dimensional radiographic image of the object.

18. The method of claim 17, wherein the radiation detector detects radiation along a transverse direction and wherein said moving comprises moving the radiation detector along a longitudinal direction that is substantially perpendicular to the transverse direction.

* * * * *